United States Patent
Kuhrs et al.

(10) Patent No.: US 7,902,411 B2
(45) Date of Patent: *Mar. 8, 2011

(54) CATALYST COMPOSITION FOR OXYCHLORINATION

(75) Inventors: Christian Kuhrs, Heidelberg (DE); Ruprecht Meissner, Weisenheim (DE)

(73) Assignee: BASF Catalysts LLC, Iselin, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/499,666

(22) Filed: Aug. 7, 2006

(65) Prior Publication Data

US 2006/0270879 A1   Nov. 30, 2006

Related U.S. Application Data

(63) Continuation of application No. 10/502,056, filed as application No. PCT/EP03/01093 on Feb. 4, 2003, now Pat. No. 7,126,035.

(30) Foreign Application Priority Data

Feb. 5, 2002 (DE) ................... 102 04 608
Aug. 7, 2002 (DE) ................... 102 36 254

(51) Int. Cl.
    C07C 17/08     (2006.01)
(52) U.S. Cl. ........................... 570/250; 502/261
(58) Field of Classification Search ............. 570/203; 502/102, 103, 104, 112
See application file for complete search history.

(56) References Cited

U.S. PATENT DOCUMENTS

| | | | |
|---|---|---|---|
| 3,420,901 A | | 1/1969 | Schulz |
| 3,504,043 A | * | 3/1970 | Yamasaki et al. ............. 570/224 |
| 4,329,527 A | | 5/1982 | Kuehn et al. |
| 4,446,249 A | | 5/1984 | Eden |
| 5,292,703 A | * | 3/1994 | Young et al. ................. 502/303 |
| 5,334,789 A | * | 8/1994 | Komatsu et al. ............. 570/203 |
| 5,347,046 A | * | 9/1994 | White et al. .................. 560/245 |
| 5,958,825 A | * | 9/1999 | Wulff-Doring et al. ...... 502/300 |
| 6,057,260 A | * | 5/2000 | Nicolau et al. ............... 502/331 |
| 6,072,078 A | * | 6/2000 | Nicolau et al. ............... 560/245 |
| 6,518,220 B2 | * | 2/2003 | Walsdorff et al. ............ 502/346 |

FOREIGN PATENT DOCUMENTS

| | | |
|---|---|---|
| EP | 0 206 265 | 12/1986 |
| EP | 0 375 202 | 6/1990 |
| EP | 0 577 059 | 1/1994 |
| EP | 0 582 165 | 2/1994 |
| EP | 0 657 212 | 6/1995 |
| FR | 2 401 891 | 3/1979 |
| GB | 1 373 296 | 11/1974 |
| GB | 1 461 846 | 1/1977 |

OTHER PUBLICATIONS

Sai Prasad et al., Parameter Estimation in a Fixed-Bed Reactor Operating under Unsteady State: Oxychlorination of Ethylene, Industrial and Engineering Chemistry Research, (2001), 40 (23), 5487-5495.*

* cited by examiner

*Primary Examiner* — Sikarl A. Witherspoon
*Assistant Examiner* — Chukwuma O Nwaonicha
(74) *Attorney, Agent, or Firm* — Oblon, Spivak, McClelland, Maier & Neustadt, L.L.P.

(57) ABSTRACT

The present invention relates to a catalyst composition for the oxychlorination of ethylene, comprising a mixture of metal salts on a support, where said metal salts are applied to the support in such ratios that the catalyst composition comprises
  a) from 3 to 12% by weight of copper as copper salt,
  b) from 0 to 3% by weight of an alkaline earth metal as alkaline earth metal salt,
  c) from 0 to 3% by weight of an alkaline metal as alkaline metal salt,
  d) from 0.001 to 0.1% by weight, preferably from 0.005 to 0.05% by weight, of at least one metal selected from the group consisting of ruthenium, rhodium, palladium, osmium, iridium and platinum, and/or from 0.0001 to 0.1% by weight, preferably from 0.001 to 0.05% by weight, of gold, as corresponding metal salt or tetrachloroauric acid, where all percentages by weight are based on the total weight of the catalyst including support material.

The invention further provides a process for preparing 1,2-dichloroethane by oxychlorination of ethylene in the presence of the above catalyst composition as catalyst.

16 Claims, No Drawings

CATALYST COMPOSITION FOR OXYCHLORINATION

The present invention relates to a catalyst composition for the oxychlorination of ethylene, comprising a mixture of metal salts on a support, where said metal salts are applied to the support in such ratios that the catalyst composition comprises from 3 to 12% by weight of copper as copper salt, from 0 to 3% by weight of an alkaline earth metal as alkaline earth metal salt, from 0 to 3% by weight of an alkali metal as alkali metal salt, from 0.001 to 0.1% by weight, preferably from 0.005 to 0.05% by weight, of at least one metal selected from the group consisting of ruthenium, rhodium, palladium, osmium, iridium and platinum, and/or from 0.0001 to 0.1% by weight, preferably from 0.001 to 0.05% by weight, of gold, as corresponding metal salt, also as tetrachloroauric acid ($HAuCl_4$) in the case of gold, where all percentages by weight are based on the total weight of the catalyst including support material.

The invention further relates to a process for preparing 1,2-dichloroethane by oxychlorination of ethylene, in which a mixture of ethylene, oxygen or oxygen-containing gas and hydrogen chloride is reacted by means of a catalyst of the above composition to form 1,2-dichloroethane.

The oxychlorination of ethylene to form 1,2-dichloroethane is a generally known process in which ethylene is reacted with hydrogen chloride and oxygen or with an oxygen-containing gas (e.g. air) in the gas phase and usually in the presence of a catalyst. Suitable catalysts generally comprise a copper compound as catalytically active component deposited on a support substance, preferably copper chloride on a support substance.

Two process in particular have become established in industry, namely a process in which the catalyst is arranged as a fixed bed and a process in which the reaction is carried out in a moving bed.

Furthermore, it is known that the presence of copper chloride alone in a catalyst composition for the oxychlorination is disadvantageous, since copper chloride is volatile at the reaction temperatures customary in oxychlorination, which leads to a loss of catalyst effectiveness over time. For this reason, the supported catalysts used usually contain promoters by means of which the effectiveness of catalytically active copper chloride on support substances is improved. These promoters include alkali metal chlorides, in particular potassium chloride and cesium chloride, alkaline earth metal chlorides, in particular magnesium chloride, or chlorides of the rare earth metals, in particular cerium chloride. For example, it has long been known that copper chloride is less volatile when it is used together with potassium chloride or sodium chloride.

Thus, EP-A 0 582 165 describes a catalyst composition comprising a support on which an active metal composition comprising from 2 to 8% by weight of copper as copper chloride, from 0.2 to 2% by weight of an alkali metal, from 0.01 to 9% by weight of a rare earth metal and from 0.05 to 4% by weight of a metal of group IIA of the Periodic Table (alkaline earth metals) is present.

EP-A 0 375 202 discloses a catalyst composition for oxychlorination, comprising a mixture of metal chlorides on a support. The mixture consists essentially of a mixture of copper chloride, magnesium chloride and potassium chloride in such ratios that the catalyst composition comprises from 3 to 9% by weight of copper, from 0.2 to 3% by weight of magnesium and from 0.2 to 3% by weight of potassium.

A similar catalytically active metal chloride composition on a support for the oxychlorination of ethylene, in which the metal chlorides are used in such ratios that the composition comprises from 3 to 9% by weight of copper, from 1 to 3% by weight of magnesium and from 0.01 to 1% by weight of potassium, is disclosed in EP-A 0 657 212.

U.S. Pat. No. 4,446,249 describes a catalytically active composition for a moving-bed catalyst in which from 0.5 to 3% by weight of at least one metal from the group consisting of potassium, lithium, rubidium, cesium, alkaline earth metals and rare earth metals or mixtures of these elements are deposited on the support substance $\gamma$-$Al_2O_3$ before the copper chloride is deposited. This is then followed by deposition of the catalytically active copper chloride on the support particles. Due to this application of the active metal components to the support substance in two steps, the catalyst particles produced by this method have less tendency to adhere to one another. This property is particularly advantageous when the catalyst is used as a moving bed.

The selectivity in which the ethylene is converted in the oxychlorination reaction into the desired end product 1,2-dichloroethane and not into the by-products which are usual in oxychlorination is greatly dependent on the catalyst composition employed. Especially in the case of reactions with a high ethylene conversion, too many by-products are still obtained when using the catalyst compositions customary hitherto.

When used as moving-bed catalysts, the particles of the customary compositions tend to stick together, which threatens the continuity of the reaction. For this reason, moving-bed catalysts for the oxychlorination of ethylene to 1,2-dichloroethane have to be optimized not only in respect of activity and selectivity but also have to display sticking-free fluidization behavior. It has been found that copper-rich catalysts have a greater tendency to stick together than low-copper catalysts.

It is an object of the present invention to provide a catalyst composition for the oxychlorination of ethylene whose use in the oxychlorination increases the conversion of the starting materials ethylene and hydrogen chloride compared to the use of the catalyst compositions customary hitherto without the selectivity for formation of 1,2-dichloroethane being reduced and without the catalyst sticking together when used as a moving bed.

We have found that this object is achieved by a catalyst composition for the oxychlorination of ethylene, comprising a mixture of metal salts on a support, where said metal salts are applied to the support in such ratios that the catalyst composition comprises a) from 3 to 12% by weight of copper as copper salt,
b) from 0 to 3% by weight of an alkaline earth metal as alkaline earth metal salt,
c) from 0 to 3% by weight of an alkali metal as alkaline metal salt,
d) from 0.001 to 0.1% by weight, preferably from 0.005 to 0.05% by weight, of at least one metal selected from the group consisting of ruthenium, rhodium, palladium, osmium, iridium and platinum, and/or from 0.0001 to 0.1% by weight, preferably from 0.001 to 0.05% by weight, of gold, as corresponding metal salt or tetrachloroauric acid, where all percentages by weight are based on the total weight of the catalyst including support material.

The presence of small amounts of a salt of the platinum metals, namely the group consisting of ruthenium, rhodium, palladium, osmium, iridium and platinum, or the presence of small amounts of appropriate gold compounds in the catalyst composition used increase the conversion of the starting materials ethylene and hydrogen chloride substantially without reducing the selectivity for the formation of 1,2-dichloroethane. As a result, a higher yield of 1,2-dichloroethane is obtained. When the catalyst is used as a moving bed, the fluidization behavior is not influenced by the addition of small amounts of the abovementioned metal salts. Metal salts of the platinum metals or of gold used in this process are preferably the corresponding oxyhalides, the oxides or the halides of the platinum metals or of gold, in particular the chlorides of the platinum metals or of gold.

The presence of a ruthenium salt, in particular the presence of ruthenium chloride, in the above-defined ratio in the catalyst composition is also preferred.

Particular preference is given to the presence of a gold salt, in particular gold chloride or tetrachloroauric acid, in the above-defined ratio in the catalyst composition.

When the catalyst compositions which have hitherto been customary are used in the oxychlorination, ethane, water, traces of hydrogen chloride and also chlorinated organic by-products plus carbon monoxide and carbon dioxide are formed as by-products. CO and $CO_2$ are present in a ratio of about 1:1. In circulation reactor processes, after removal of the main product 1,2-dichloroethane from the product gas stream, some of these by-products of the oxychlorination are condensed out and some are usually discharged from the process via a purge stream. The remaining product gas which comprises as yet unreacted starting material, in particular ethylene, is subsequently recirculated to the reactor. However, removal of by-products via a purge stream also results in small losses of 1,2-dichloroethane, the main product. Avoiding formation of CO could offer advantages in the work-up of offgas or recycle gas streams, since $CO_2$ can be scrubbed out more readily than CO.

The use of a catalyst composition according to the present invention in the oxychlorination therefore offers not only the advantage of an increase in the yield of 1,2-dichloroethane when a promoter from the group consisting of the platinum metals is used but also the further advantage that only very small amounts of carbon monoxide are formed while carbon dioxide is formed as virtually exclusive by-product.

As support substance for the catalyst composition of the present invention, it is possible to use aluminum oxide, silica gel, pumice and clay. Preference is given to using aluminum oxide as support substance. The specific surface area of the support substance before deposition of the metal salt is preferably in the range from 20 to 400 $m^2/g$, more preferably from 75 to 200 $m^2/g$. Customary support substances for oxychlorination catalysts preferably have a pore volume in the range from 0.15 to 0.75 $cm^3/g$, and the average particle sizes are preferably in the range from 30 to 500 μm. In the support substances used here, the proportion of particles having a diameter of less than 45 μm is 30% or 5%, with the BET surface areas being 170 $m^2/g$ or 150 $m^2/g$.

The invention further provides a process for preparing 1,2-dichloroethane by oxychlorination of ethylene in the presence of a catalyst composition according to the present invention as catalyst.

The process of the present invention for preparing 1,2-dichloroethane can be carried out using the known techniques and reaction conditions which are generally customary according to the prior art. Ethylene, hydrogen chloride and molecular oxygen in the gas phase are brought into contact with a catalyst composition according to the present invention at from 80 to 300° C., preferably from 210 to 260° C. The molecular oxygen can be introduced as such or in the form of an oxygen-containing gas mixture, e.g. air. In the case of circulation reactor processes (gas recycle mode) in which unreacted starting material is recirculated to the reactor, only pure oxygen is used.

The molar ratios of the starting materials used in the process of the present invention are generally from 5:1 to 3:1, preferably about 4:1, for hydrogen chloride:oxygen and generally about 1:2 for ethylene:hydrogen chloride. The hydrogen chloride is preferably present in a slightly substoichiometric amount based on the reaction $2C_2H_4+4HCl+O_2 \rightarrow 2C_2H_4Cl_2+2H_2O$, so that it is ensured that hydrogen chloride is virtually completely reacted in one pass through the reactor. In the gas recycle mode, ethylene is fed in in a still higher excess. The ethylene:HCl:$O_2$ ratio is preferably chosen so that ethylene, too, is very substantially reacted in one pass through the reactor. The reaction pressure is in the range from 1 to 20 bar, preferably from 1 to 8 bar.

The material of construction used for the reactor is usually based on iron (stainless steel) or a nickel alloy. When an oxychlorination reaction is carried out on a small scale, glass can also be used as reactor material.

In the process of the present invention, the catalyst can be used either as a fixed bed or as a moving bed. If the catalyst is used as a moving bed in the process of the present invention, it is preferably in a fluidized state. This is generally achieved at velocities in the range from 1 to 100 cm/s. If the catalyst is used as a fixed bed in the process of the present invention, it is preferably used in the form of hollow cylinders or annular pellets whose end faces are rounded both on the outer edge and on the edge of the central holes. This preferred form of fixed-bed catalyst can be made up of either hollow cylinders or annular pellets composed of catalytically active material or preferably support material in the shape of hollow cylinders or annular pellets to which a catalytically active composition has been applied. The external diameter of the catalyst hollow cylinders or annular pellets is from 3 to 20 mm, preferably from 3 to 10 mm, particularly preferably from 3 to 7 mm, in particular from 3.5 to 6.5 mm, and the internal diameter is from 0.1 to 0.7 times the external diameter. The length of the catalyst hollow cylinders or annular pellets is from 0.2 to 2 times, preferably from 0.3 to 1.8 times, particularly preferably from 0.4 to 1.6 times, the external diameter. The radius of curvature of the end faces is from 0.01 to 0.5 times, preferably from 0.05 to 0.4 times, particularly preferably from 0.1 to 0.2 times, the external diameter. These catalyst shapes, which are described in EP 1 127 618 A1, give a particularly low pressure drop and display good mechanical strength and are particularly suitable for use in strongly exothermic reactions such as the oxychlorination of ethylene.

Fixed-bed catalysts having a shape as described in EP 1 127 618 A1 are thus an integral part of the present invention and are incorporated by reference.

The invention further provides a catalyst for preparing 1,2-dichloroethane by oxychlorination of ethylene in the presence of a fixed-bed catalyst having a composition according to the present invention and, if desired, a shape as described in EP 1 127 618 A1.

To prepare an aqueous solution for impregnating the support substance, the required amounts of the appropriate metal compounds, preferably in the form of their hydrates, are dissolved in water. The aqueous solution is then applied to the support substance. The support substance which has been impregnated in this way is subsequently filtered off from the remaining aqueous phase if necessary and finally dried. Filtration is not necessary when the support substance is brought into contact with a volume of the aqueous solution which is no greater than that sufficient for saturating the support substance.

The present invention is illustrated by the following examples.

EXAMPLE 1

A catalyst composition according to the present invention was produced by impregnating the support substance with an aqueous solution obtained as follows:

86.4 g of $CuCl*2H_2O$, 89.8 g of $MgCl*6H_2O$, 5.5 g of KCl and 0.2 g of $RuCl_3*H_2O$ were dissolved in a small amount of water. Further water was added until a total volume of 300 ml, corresponding to the maximum water absorption capacity of the amount of support substance used, was obtained. This metal chloride solution was added to 600 g of an aluminum oxide support having a proportion of particles smaller than 45 μm of 30% and a BET surface area of 170 $m^2/g$. After stirring for one hour, the mixture was dried at 110° C. for 16 hours in the presence of nitrogen to give a catalyst A containing 4.5% by weight of Cu, 1.5% by weight of Mg, 0.4% by weight of K and 0.01% by weight of Ru.

For comparison, a catalyst composition having the same proportions by weight of copper chloride, magnesium chloride and potassium chloride but without ruthenium chloride was produced in the same way (catalyst B).

Both oxychlorination catalysts (catalyst A and B) were installed in a moving-bed reactor made of glass into which the starting materials ethylene, air and hydrogen chloride were fed and which was maintained at a bed temperature of 232° C., 243° C. or 254° C. The reactor was operated at a pressure of 4 bar using an amount of 500 g of the catalyst of the appropriate composition. In each case, 119 standard l/h of air, 69.9 standard l/h of hydrogen chloride and 35.5 standard l/h of ethylene were fed to the reactor, which gave a space velocity of 160 g of cat./(mol of HCl h-1). The products formed in each case were analyzed by means of gas chromatography.

The results are collated in the table below.

Comparison of the results shows that the presence of small amounts of ruthenium chloride in the catalyst composition used increases the conversion of both hydrogen chloride and ethylene at the various reaction temperatures without reducing the selectivity to 1,2-dichloroethane (see table below). This is reflected in a significant increase in the yield of 1,2-dichloroethane when using the catalyst composition of the present invention (here catalyst A).

In addition, the results show that the formation of carbon monoxide as by-product is suppressed effectively when using the catalyst composition of the present invention.

EXAMPLE 2

A further catalyst composition according to the present invention was produced in a manner similar to example 1 but using palladium chloride as promoter instead of ruthenium chloride to give catalyst C containing 4.5% by weight of Cu, 1.5% by weight of Mg, 0.4% by weight of K and 0.01% by weight of Pd.

The results are collated in the table below. They clearly show the effect of palladium, which is comparable to that of ruthenium both in respect of the increase in activity and also in respect of the suppression of CO formation.

EXAMPLE 3

A further catalyst composition according to the present invention was produced in a manner similar to example 1 but using gold chloride as promoter instead of ruthenium chloride to give catalyst D containing 4.5% by weight of Cu, 1.5% by weight of Mg, 0.4% by weight of K and 0.005% by weight of Au.

The results are collated in the table below. They clearly show the effect of gold, which increases the activity to a greater extent than do ruthenium and palladium, particularly at the two lower temperatures.

TABLE

| Catalyst | Temp. (° C.) | HCl conversion (%) | Ethylene conversion (%) | EDC selectivity (%) | EDC yield (%) | CO selectivity (%) | $CO_2$ selectivity (%) | Selectivity to formation of chlorinated by-products (total, %) |
|---|---|---|---|---|---|---|---|---|
| A | 254 | 98.93 | 98.54 | 95.87 | 94.47 | 0.07 | 2.17 | 1.88 |
| A | 243 | 97.42 | 96.48 | 97.41 | 93.98 | 0.06 | 1.22 | 1.31 |
| A | 232 | 93.41 | 91.97 | 98.26 | 90.37 | 0.03 | 0.51 | 1.20 |
| B | 254 | 97.90 | 97.42 | 96.08 | 93.60 | 1.04 | 1.00 | 1.88 |
| B | 243 | 95.18 | 94.37 | 97.41 | 91.93 | 0.84 | 0.52 | 1.22 |
| B | 232 | 89.19 | 88.21 | 98.55 | 86.94 | 0.53 | 0.23 | 0.68 |
| C | 254 | 98.81 | 98.71 | 95.78 | 94.55 | 0.13 | 2.32 | 1.77 |
| C | 243 | 97.60 | 97.11 | 97.27 | 94.46 | 0.29 | 1.36 | 1.08 |
| C | 232 | 96.21 | 94.34 | 97.86 | 92.32 | 0.19 | 0.80 | 1.15 |
| D | 254 | 99.54 | 99.02 | 95.22 | 94.28 | 1.04 | 1.32 | 2.43 |
| D | 243 | 98.82 | 98.00 | 97.26 | 95.31 | 0.69 | 0.77 | 1.27 |
| D | 232 | 96.68 | 95.90 | 98.28 | 94.25 | 0.49 | 0.53 | 0.69 |

We claim:

1. A process for preparing 1,2-dichloroethane, comprising oxychlorinating ethylene in the presence of a catalyst composition, wherein ethylene, hydrogen chloride and molecular oxygen in the gas phase are brought into contact with the catalyst composition at from 210 to 260° C., said catalyst composition comprising a mixture of metal salts on a support, where said metal salts are applied to the support in such ratios that the catalyst composition comprises
   a) from 3 to 12% by weight of copper as copper salt,
   b) from 0 to 3% by weight of an alkaline earth metal as alkaline earth metal salt,
   c) from 0 to 3% by weight of an alkaline metal as alkaline metal salt,
   d) from 0.001 to 0.1% by weight, of at least one metal selected from the group consisting of ruthenium, rhodium, palladium, osmium, iridium and platinum, and/or from 0.0001 to 0.1% by weight, of gold, as corresponding metal salt or tetrachloroauric acid,
   wherein all percentages by weight are based on the total weight of the catalyst including support material.

2. The process as claimed in claim 1, which is a circulation reactor process.

3. The process as claimed in claim 1, wherein the catalyst is used as a moving bed.

4. The process as claimed in claim 1, wherein the catalyst is used as a fixed bed.

5. The process as claimed in claim 4, wherein the catalyst is used as a fixed bed in the form of hollow cylinders or annular pellets whose end faces are rounded both to the outer edge and to the central holes.

6. The process as claimed in claim 1, wherein the catalyst composition comprises from 0.005 to 0.05% by weight of at least one metal selected from the group consisting of ruthenium, rhodium, palladium, osmium, iridium and platinum.

7. The process as claimed in claim 1, wherein the catalyst composition comprises from 0.001 to 0.05% by weight of gold.

8. The process as claimed in claim 1, wherein the metal salts are selected from among metal halides, metal oxyhalides and metal oxides of the respective metal and tetrachloroauric acid.

9. The process as claimed in claim 8, wherein the metal halides of the respective metal are metal chlorides.

10. The process as claimed in claim 1, wherein the component d) used is a ruthenium salt or a gold salt.

11. The process as claimed in claim 1, wherein the component b) used is a magnesium salt.

12. The process as claimed in claim 1, wherein the component c) used is a potassium salt.

13. The process as claimed in claim 1, wherein the support used is aluminum oxide.

14. The process as claimed in claim 1, wherein the support has a pore volume in the range from 0.15 to 0.75 $cm^3/g$.

15. The process as claimed in claim 1, wherein the specific surface area of the support used is in the range from 20 to 400 $m^2/g$.

16. The process as claimed in claim 1, wherein the catalyst composition comprises from 0.005 to 0.05% by weight of at least one metal selected from the group consisting of ruthenium, rhodium, palladium, osmium, iridium and platinum, and/or from 0.001 to 0.05% by weight, of gold, as corresponding metal salt or tetrachloroauric acid.

* * * * *